US011243415B2

(12) United States Patent
Lee

(10) Patent No.: US 11,243,415 B2
(45) Date of Patent: Feb. 8, 2022

(54) EYE CONVERGENCE DETECTION WITH CONTACT LENSES

(71) Applicant: Verily Life Sciences LLC, South San Francisco, CA (US)

(72) Inventor: Shungneng Lee, Sunnyvale, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 130 days.

(21) Appl. No.: 16/370,618

(22) Filed: Mar. 29, 2019

(65) Prior Publication Data

US 2019/0227345 A1 Jul. 25, 2019

Related U.S. Application Data

(62) Division of application No. 14/873,034, filed on Oct. 1, 2015, now Pat. No. 10,281,743.

(51) Int. Cl.
*G02C 7/08* (2006.01)
*G02C 7/04* (2006.01)
(Continued)

(52) U.S. Cl.
CPC ............. *G02C 7/083* (2013.01); *A61B 3/10* (2013.01); *A61B 3/113* (2013.01);
(Continued)

(58) Field of Classification Search
CPC .......... G02C 7/083; G02C 7/04; G02C 11/10; G02B 27/0093; A61B 3/10; A61B 3/113
See application file for complete search history.

(56) References Cited

U.S. PATENT DOCUMENTS

| 6,163,281 A | 12/2000 | Torch |
| 7,018,040 B2 | 3/2006 | Blum et al. |

(Continued)

FOREIGN PATENT DOCUMENTS

| EP | 1941829 A2 | 7/2008 |
| EP | 2772789 A1 | 9/2014 |

(Continued)

OTHER PUBLICATIONS

First Office Action for Chinese Patent Application No. 201680057900.7, dated Feb. 9, 2019, 30 pages.

(Continued)

*Primary Examiner* — Tuyen Tra
(74) *Attorney, Agent, or Firm* — Christensen O'Connor Johnson Kindness PLLC

(57) ABSTRACT

A contact lens, system of contact lenses, and a method for detecting eye convergence includes detecting a first inward gaze with first gaze detection circuitry included in a first contact lens disposed on a first eye. A first inward gaze signal is transmitted from the first contact lens to a second contact lens disposed in a second eye in response to detecting the first inward gaze. A second inward gaze is detected with second gaze detection circuitry included in a second contact lens disposed on the second eye. The first inward gaze signal is received by the second contact lens. If the first inward gaze signal is received within a pre-determined time period from detecting the second inward gaze, an optical power for the second eye is adjusted.

9 Claims, 9 Drawing Sheets

(51) Int. Cl.
*G02C 11/00* (2006.01)
*G02B 27/00* (2006.01)
*A61B 3/10* (2006.01)
*A61B 3/113* (2006.01)

(52) U.S. Cl.
CPC .......... *G02B 27/0093* (2013.01); *G02C 7/04* (2013.01); *G02C 11/10* (2013.01)

(56) References Cited

U.S. PATENT DOCUMENTS

| | | | |
|---|---|---|---|
| 8,786,675 B2 | 7/2014 | Deering | |
| 8,820,934 B1 * | 9/2014 | Ho | G02C 7/04 351/219 |
| 9,050,185 B2 | 6/2015 | Pugh et al. | |
| 9,063,351 B1 | 6/2015 | Ho et al. | |
| 9,072,465 B2 | 7/2015 | Pugh et al. | |
| 10,222,632 B2 | 3/2019 | Lee | |
| 11,022,819 B2 | 6/2021 | Lee | |
| 2012/0140167 A1 | 6/2012 | Blum | |
| 2012/0245444 A1 | 9/2012 | Otis et al. | |
| 2013/0225968 A1 | 8/2013 | Auvray et al. | |
| 2013/0258275 A1 | 10/2013 | Toner et al. | |
| 2014/0022505 A1 | 1/2014 | Pugh et al. | |
| 2014/0081178 A1 | 3/2014 | Pletcher et al. | |
| 2014/0118829 A1 | 5/2014 | Ma et al. | |
| 2014/0156000 A1 | 6/2014 | Campin et al. | |
| 2014/0240655 A1 | 8/2014 | Pugh et al. | |
| 2014/0240656 A1 | 8/2014 | Pugh et al. | |
| 2014/0240665 A1 | 8/2014 | Pugh et al. | |
| 2014/0327875 A1 | 11/2014 | Blum et al. | |
| 2015/0005750 A1 | 1/2015 | Kelleher et al. | |
| 2015/0061999 A1 | 3/2015 | Kim et al. | |
| 2015/0062533 A1 | 3/2015 | Toner et al. | |
| 2015/0173658 A1 | 6/2015 | Liu et al. | |
| 2015/0185504 A1 | 7/2015 | Peloux | |
| 2015/0215601 A1 | 7/2015 | Zhou | |
| 2015/0362756 A1 | 12/2015 | Wiser et al. | |
| 2017/0031159 A1 | 2/2017 | Pugh et al. | |
| 2017/0092235 A1 | 3/2017 | Osman et al. | |
| 2017/0112433 A1 | 4/2017 | Pugh et al. | |
| 2017/0097520 A1 | 5/2017 | Lee | |
| 2017/0192502 A1 | 7/2017 | Dmitrieva et al. | |
| 2017/0227792 A1 | 8/2017 | Starner et al. | |
| 2018/0035882 A1 | 2/2018 | Gutierrez et al. | |
| 2018/0217402 A1 | 8/2018 | Larmagnac et al. | |

FOREIGN PATENT DOCUMENTS

| | | |
|---|---|---|
| EP | 2772792 A1 | 9/2014 |
| EP | 2846183 A2 | 3/2015 |
| EP | 2851738 A2 | 3/2015 |
| EP | 3125021 A1 | 2/2017 |
| WO | 2009081343 A1 | 7/2009 |
| WO | 2013112080 A1 | 8/2013 |
| WO | 2014129918 A1 | 8/2014 |
| WO | 2014194432 A1 | 12/2014 |
| WO | 2015191241 A1 | 12/2015 |
| WO | 2015194120 A1 | 12/2015 |

OTHER PUBLICATIONS

PCT/US2016/048205—International Search Report and Written Opinion, dated Feb. 15, 2017, 16 pages.
First Office Action for Chinese Patent Application No. 2016800583962 dated Feb. 2, 2019, 31 pages.
First Examination Report for European Patent Application No. 16764004.4 dated Apr. 3, 2019, 3 pages.
Examination Report in corresponding EP Patent Application No. 16764004.4-1020, dated Dec. 17, 2019, 4 pages.
International Search Report and Written Opinion dated Nov. 24, 2016, in International Patent Application No. PCT/US2016/048204, 15 pages.
International Search Report and Written Opinion, dated May 11, 2017, in International Patent Application No. PCT/US2017/016850, 9 pages.

* cited by examiner

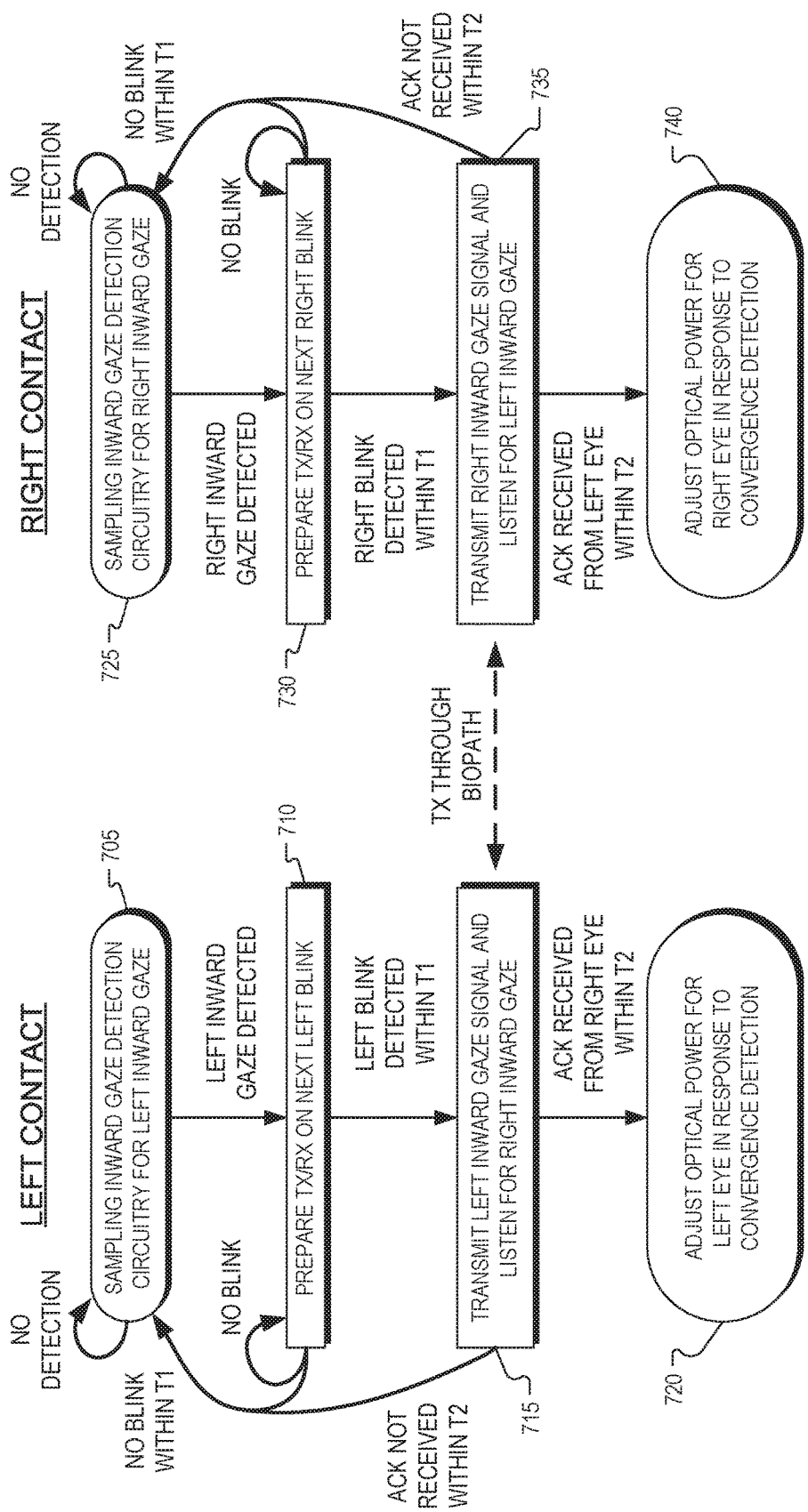

EYE CONVERGENCE DETECTION WITH CONTACT LENSES

CROSS REFERENCE TO RELATED APPLICATION

The present application is a divisional of U.S. application Ser. No. 14/873,034, filed on Oct. 1, 2015, the contents of which are hereby incorporated by reference. The present application is also related to U.S. application Ser. No. 14/873,025, filed on Oct. 1, 2015, entitled "Lens-to-Lens Communication for Contact Lenses."

TECHNICAL FIELD

This disclosure relates generally to contact lenses, and in particular to eye convergence detection with contact lenses.

BACKGROUND INFORMATION

Contact lenses have been developed that include on-board measurement sensors. When worn by a user, contact lenses have access to measure biometric data through the tear solution of the eye, for example. Contact lenses are also in position to measure a gaze direction of a user. In certain contexts, it is desirable for data from the measurements to be accessible by the contact lens worn in the opposite eye. Other contact use cases would also benefit from lens-to-lens communication between contact lenses. However, conventional technologies generally require the user/wearer to manually bring additional hardware into proximity with a pair of contacts to share data between contact lenses. Having additional hardware required for lens-to-lens communication reduces the contexts and functionality of contact lenses that would benefit from lens-to-lens communication.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

FIG. 7 illustrates a second flow chart for an example process of detecting eye convergence using lens-to-lens communication, in accordance with an embodiment of the disclosure.

DETAILED DESCRIPTION

Embodiments of a system and method for detecting eye convergence with contact lenses are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
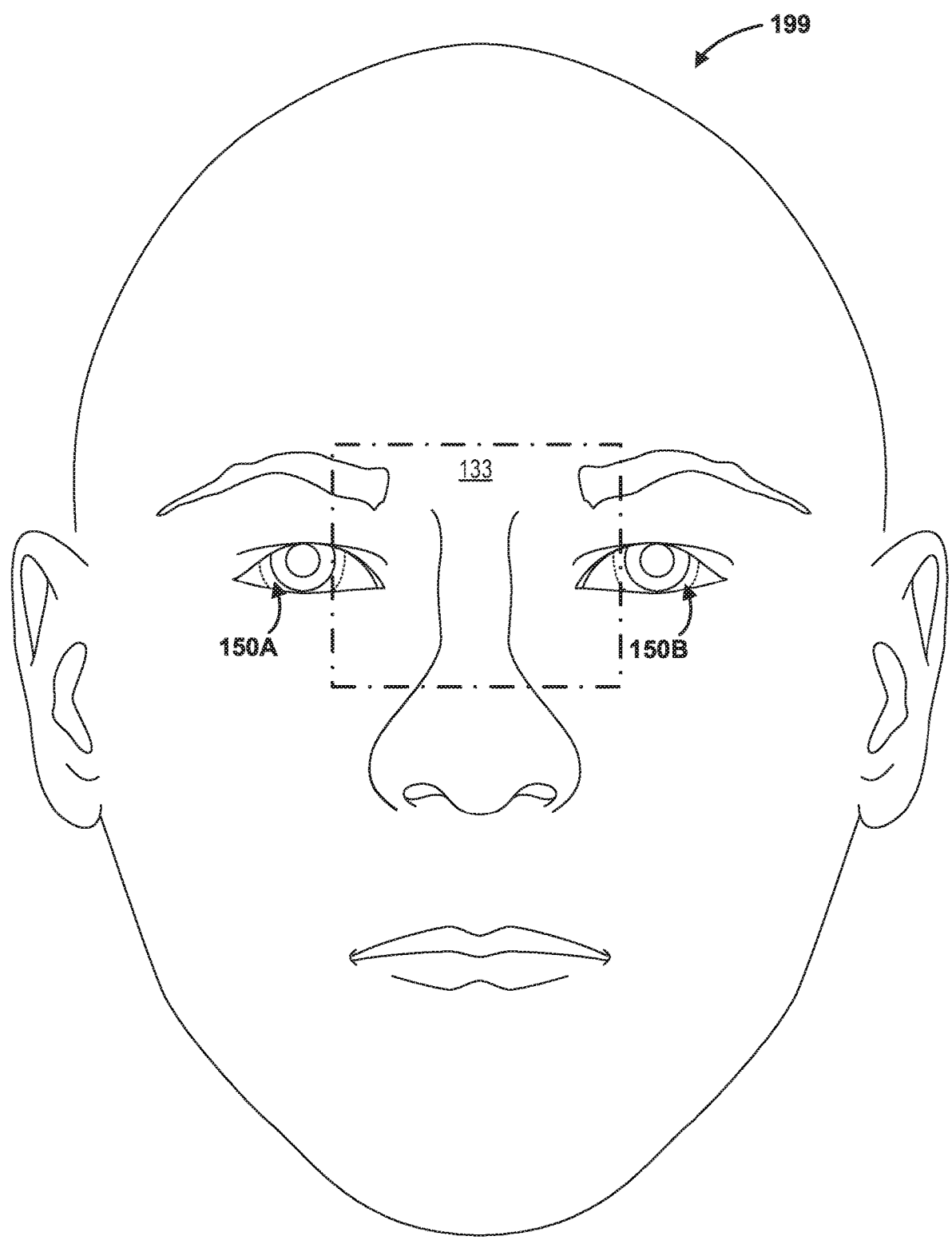
FIG. 1 illustrates a user wearing a pair of contact lenses that form a lens-to-lens communication system, in accordance with an embodiment of the disclosure.

FIG. 1 illustrates a user 199 wearing a pair of contact lenses that form a lens-to-lens communication system, in accordance with an embodiment of the disclosure. User 199 is wearing a pair of contact lenses that includes a right contact lens 150A and a left contact lens 150B. Contact lenses 150A and 150B communicate by using biopath 133 as a signal path for low power signals. This disclosure describes lens-to-lens communication between contact lenses and also describes certain use cases for lens-to-lens communication. In some cases, the lens-to-lens communication will be during a blinking of eyes of user 199. A blink of a human eye typically is not less than 100 ms. Blinking is typically synchronized in that both eye blink at the same time. Hence, a detection of a blink can be an advantageous time to establish a reference time for data transmission between contact lenses.

Figure 2:
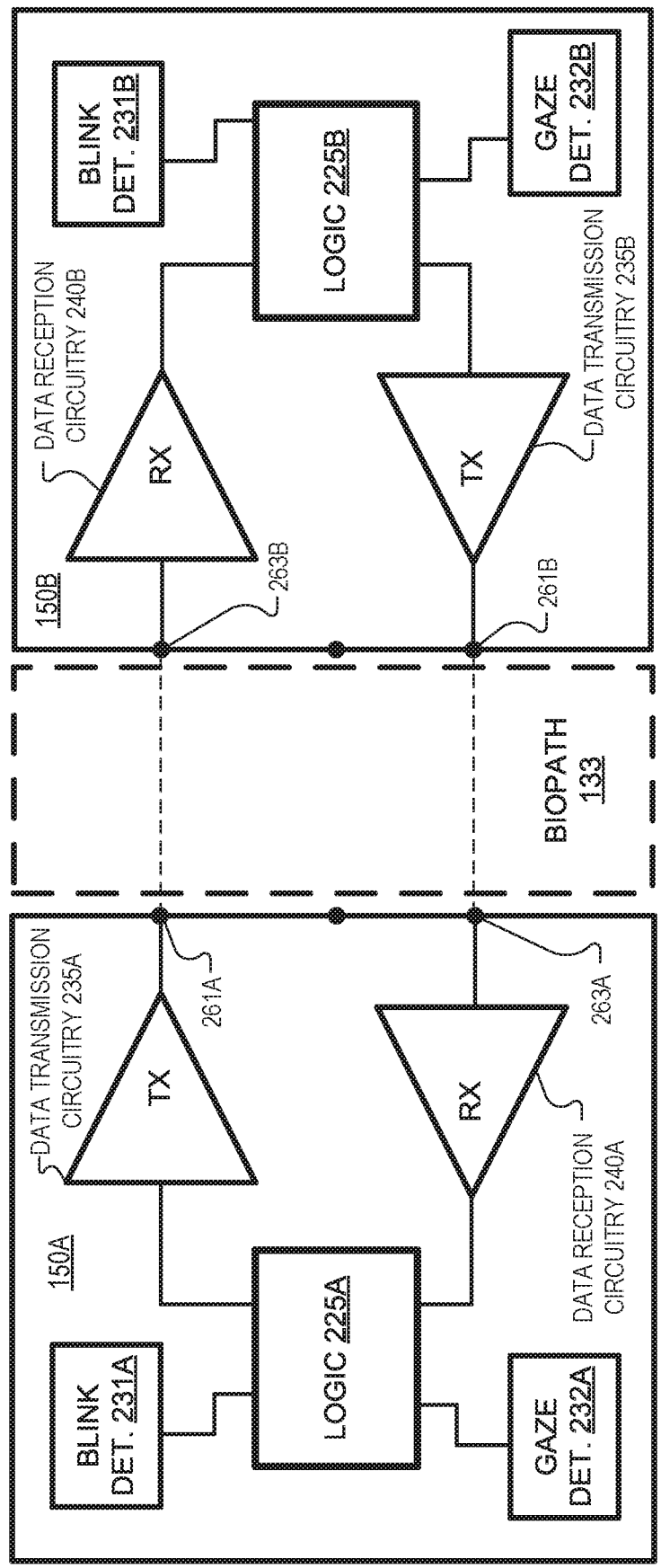
FIG. 2 illustrates a block diagram schematic that includes contact lenses having transmission and reception circuitry for lens-to-lens communication, in accordance with an embodiment of the disclosure.

FIG. 2 illustrates a block diagram schematic of a system 200 that includes contact lenses 150A and 150B. In FIG. 2, contact lenses 150 include logic engine 225, data transmission circuitry 235, data reception circuitry 240, blink detection circuitry 231, and gaze detection circuitry 232. Not all embodiments will necessarily include all of the elements illustrated in contact lenses 150.

Logic engine 225 may include a microprocessor, a Field Programmable Gate Array ("FPGA"), or other discrete logic. Logic engine 225 may be fabricated utilizing CMOS processing techniques into a semiconductor substrate of contact lens 150. Logic engine 225 may include memory to store settings, instructions, and/or data received from circuitry of contact lens 150. Logic engine 225 is coupled to receive a blink signal from blink detection circuitry 231. Blink detection circuitry 231 is configured to generate the blink signal in response to an eye blinking or closing (when contact 150 is inserted into an eye). Logic engine 225 is also coupled to receive an inward gaze signal from gaze detection circuitry 232. Gaze detection circuitry is configured to generate an inward gaze signal in response to an eye looking inward (when contact 150 is inserted into an eye). Looking "inward" is looking inward toward the nose of a wearer of contact lens 150.

Figure 3A:
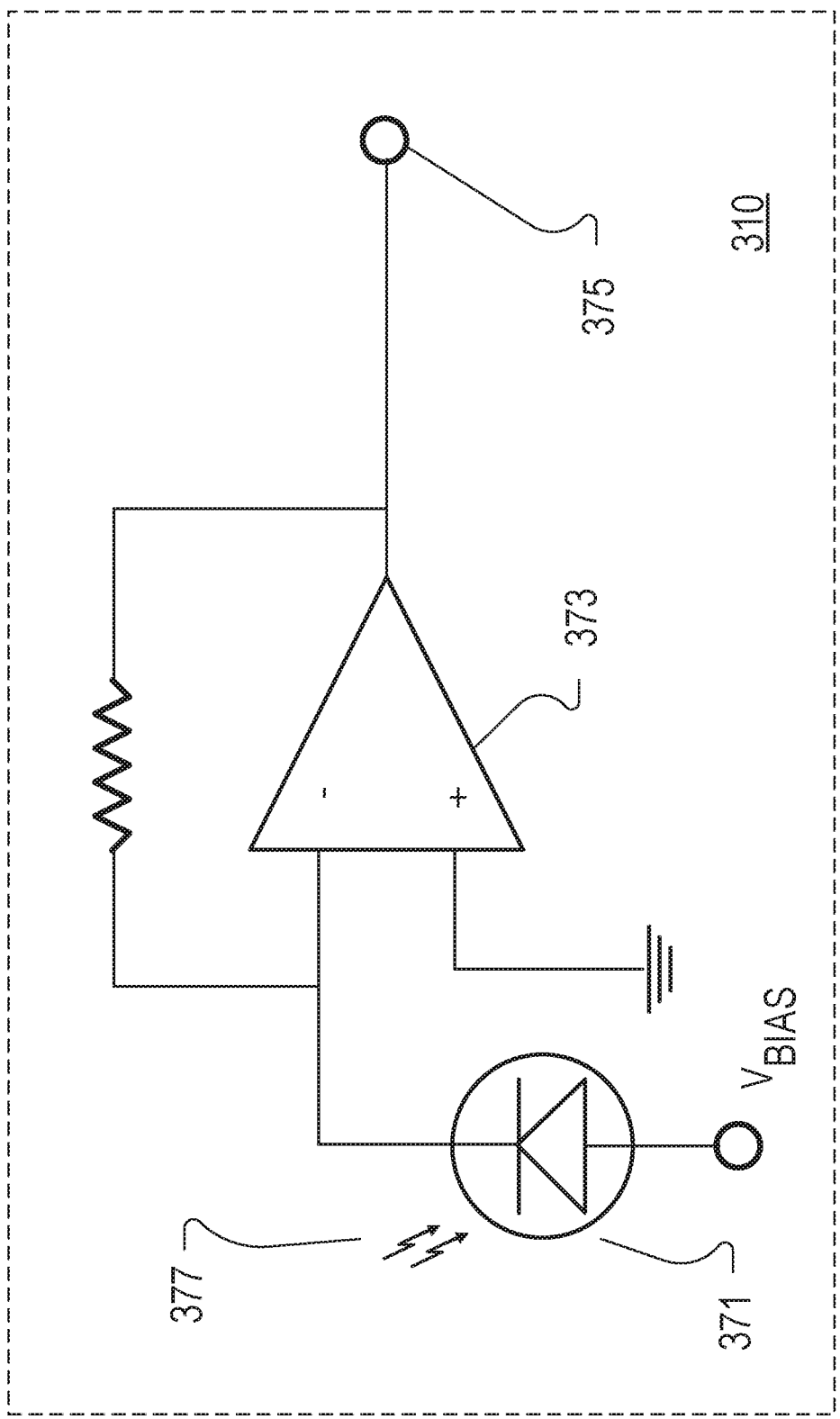
FIG. 3A illustrates one example of blink detection circuitry that includes a photodiode, in accordance with an embodiment of the disclosure.

Logic engine 225 is configured to cause data transmission circuitry 235 to drive electrical signals onto electrode 261 in response to the blink signal from blink detection circuitry 231 reaching a pre-determined threshold. FIG. 3A illustrates blink detection circuitry 310 that could be used as blink detection circuitry 231, in accordance with an embodiment of the disclosure. Blink detection circuitry 310 includes a photodiode or photosensor 371, amplifier 373, and output node 375. Amplifier 373 generates the blink signal on node 375 in response to a current generated by photodiode 371 in response to ambient light 377 incident on photodiode 371. The blink signal increases when the incident ambient light 377 increases in intensity and the blink signal decreases when incident ambient light 377 decreases, in FIG. 3A. When a wearer of contact 150 closes the eye that the contact 150 is worn in, the photodiode will receive very little (if any) ambient light 377. In one embodiment, logic engine 225 causes data transmission circuitry 235 to send the electrical data signals when a voltage on node 375 falls below a pre-determined threshold and recovers above the pre-determined threshold under a pre-determined amount of time (e.g. 400 ms) that would signify a blink.

In another embodiment, blink detection circuitry 231 includes sensing electrodes that are exposed to be contacted by an eyelid when an eye blinks, but the sensing electrodes are not contacted by the eyelid when the eye is open (viewing the world). In this embodiment, logic engine 225 measures an electrical impedance between the sensing electrodes to detect an eye blink. When the eyelid is open, the electrical impedance magnitude between the sensing electrodes will be very high (open circuit) since the eyelid will not be contacting the sensing electrodes. The eyelid closing will put a measurable electrical impedance across the sensing electrode as the eyelid contacts both sensing electrodes and closes the circuit.

When logic engine 225 detects that the eye has closed, it drives data transmission circuitry 235 to transmit electrical data signals onto electrode 261 and ultimately through biopath 133. The electrical data signals are short pulses, in one embodiment. In one embodiment, the pulses are 400 mV and 10 ns in duration. A variety of different communication protocols can be utilized to communicate data between contacting lenses using low voltage pulses as bits.

Figure 3B:
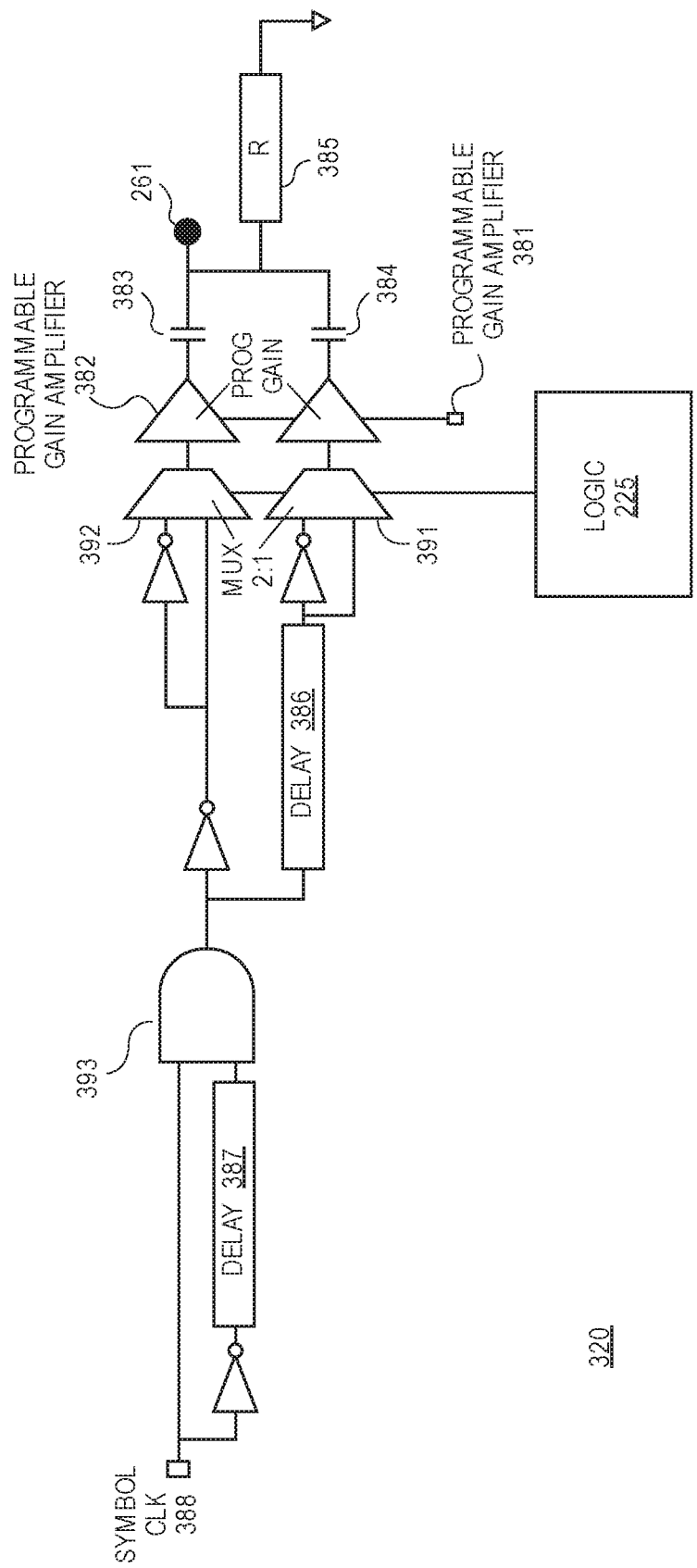
FIG. 3B illustrates one example of data transmission circuitry for a contact lens, in accordance with an embodiment of the disclosure.

FIG. 3B illustrates one example of data transmission circuitry 320 for a contact lens, in accordance with an embodiment of the disclosure. Data transmission circuitry 320 is one example of data transmission circuitry 235. Data transmission circuitry 320 is a transmitter for Binary phase-shift keying ("BPSK") signaling. It is appreciated that data transmission circuitry 235 may be incorporated into logic engine 225, in some embodiments.

Data transmission circuitry 320 includes programmable delays 386 and 387, AND gate 393, 2:1 multiplexors 391 and 392, programmable gain amplifiers 381 and 382, capacitors 383 and 384, and resistor 385. Symbol CLK 388 is a clock coming in at the pulse repetition frequency, or whenever a pulse is required. The pulse is generated at the output of AND gate 393 at the rising edge of symbol CLK 388. At every positive edge of symbol CLK 388, a pair of antipodal pulses is generated at terminal 261. The first programmable delay 387 on the left dictates the width of a pulse within a pair of pulses. One pair of antipodal pulses is equivalent to one pulse bit symbol signal. This can be a delay line created with a cascade of a current starved inverter. The second programmable delay 386 dictates the pulse separation time between pulses within a symbol. This depends on the typical channel impulse response, and can be programmed so that there is no inter-pulse interference within a symbol. Muxes 391/392 take as inputs different types of pulses: the upper mux 392 is responsible for selecting the sign of the first pulse in a pair of pulses that form a bit symbol, and the lower mux 391 is responsible for selecting the sign of the second pulse in a pair of pulses that form a bit.

The programmable gain stages 381/382 allow the digital pulses that come out of muxes 391/392 to be converted to analog, and these stages dictate the amplitude of the pulses. Capacitors 383/384 are summing capacitors that combine the two pulses differing in time and sign to terminal 261. Resistor 385 is a large resistor that sets the DC bias of terminal 261 to zero. The pulses are generated in pairs of pulses, the pulses are opposite in sign, and carry zero net charge over the symbol (resistor to ground and equivalent but opposite in sign pulses going into the capacitors 383/384 will ensure that). Logic engine 225 is coupled to muxes 391/392. By driving a digital high or low onto muxes 391/392, logic engine 225 can generate positive or negative pulses.

In one embodiment, electrode 261 is disposed to come in contact with a tear film of an eye to transmit electrical data signals. In one embodiment, electrode 261 is encapsulated within a contact lens and disposed to be capacitively coupled to transmit electrical data signals to a tear solution of the eye. Electrode 263 may be encapsulated within a contact lens and disposed to be capacitively coupled to receive a raw data signal from a tear solution of the eye or disposed to come in contact with the tear film to receive the raw data signal.

The electrical data signals travel from electrode 261 through biopath 133 to reach data reception circuitry 240B via electrode 263. Biopath 133 includes biological matter disposed between the human eye and in particular the biological matter in the path between electrodes 261 and 263.

Figure 3C:
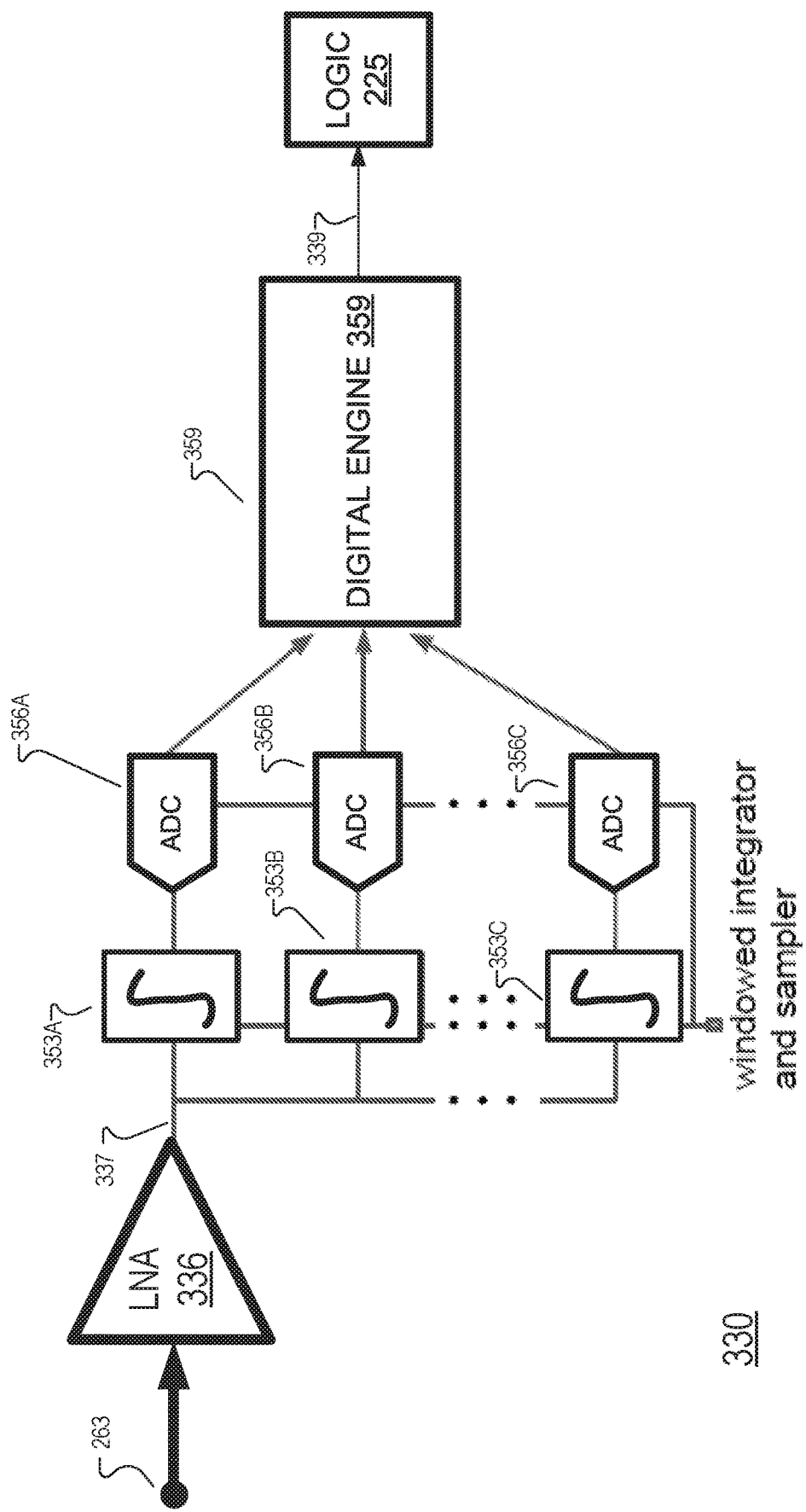
FIG. 3C illustrates one example of data reception circuitry for a contact lens, in accordance with an embodiment of the disclosure.

FIG. 3C illustrates one example of data reception circuitry for a contact lens, in accordance with an embodiment of the disclosure. Data reception circuitry 330 is one example of data reception circuitry 240. Data reception circuitry 330 is a receiver for BPSK signaling. Data reception circuitry 330 includes low-noise-amplifier (LNA) 336, windowed integrators 353, Analog-to-Digital Converters ("ADCs") 356, and Digital Engine 359. Windowed integrators 353, Analog-to-Digital Converters ("ADCs") 356, and Digital Engine 359 may be considered to form a mixed-signal correlator. The electrical data signals driven onto electrode 261 are received as raw data signals at electrode 263 and LNA 336. LNA 336 amplifies the raw data signal into an amplified data signal 337. Interleaved windowed integrators 353 shuffle and integrate the LNA output 337 onto a bank of integrating capacitors (not illustrated) whose structure and multiplicity (number of windowed integrators that will be shuffled in/out) will be optimized for efficiency and power. ADCs 356 are coupled to sample the analog integration value to digital and Digital Engine 359 generates output data 339 by performing timing, channel, and bit recovery on the digital outputs of ADCs 356. In one embodiment, an inverse transform is performed to reconstruct the electrical data signal(s) that was driven onto electrode 261. The inverse transform of the amplified data signal 337 may be informed by an impedance-based channel modeling of biopath 133.

In the illustrated embodiment of system 200, each contact lens has both data transmission circuitry 235 and data reception circuitry 240 to enable bi-directional communication. However, in one embodiment of system 200, one contact lens (e.g. lens 150A) has data transmission circuitry 235, but not data reception circuitry 240 and the other contact lens (e.g. lens 150B) has data reception circuitry 240, but not data transmission circuitry 235. In this embodiment, the communication between contact lenses in unidirectional.

Figure 4A:
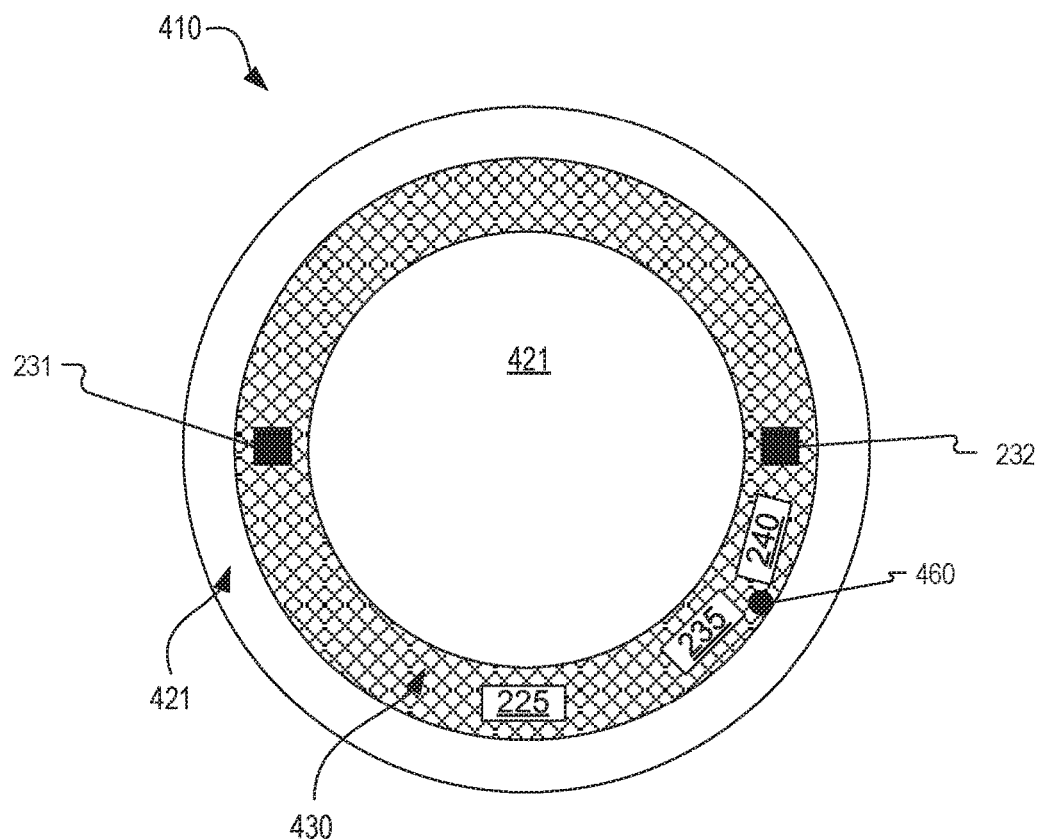
FIG. 4A illustrates a top view of an example contact lens for lens-to-lens communication, in accordance with an embodiment of the disclosure.

FIG. 4A illustrates a top view of a contact lens 410 that includes logic engine 225, data transmission circuitry 235, data reception circuitry 240, blink detection circuitry 231, and gaze detection circuitry 232, in accordance with an embodiment of the disclosure. Contact lens 410 is one example of contact lenses 150. Contact lens 410 includes transparent material 421 that is made from a biocompatible material suitable for a contact lens. In one embodiment, the contact lens includes a silicone elastomer. In one embodiment, the contact lens includes hydrogel. Substrate 430 is illustrated as a substantially flattened ring disposed atop or embedded within transparent material 421. In one embodiment, the flattened ring has a diameter of about 10 millimeters, a radial width of about 1 millimeter, and a thickness of about 50 micrometers.

Substrate 430 includes one or more surfaces for mounting elements such as logic engine 225, data transmission circuitry 235, data reception circuitry 240, blink detection circuitry 231, and gaze detection circuitry 232. In one embodiment, substrate 430 includes a semiconductor material (e.g. silicon) and logic engine 225 is formed in substrate 430 by way of common CMOS processes. In one embodiment, substrate 430 includes a multi-layer flexible circuit board. In one embodiment, substrate 430 is made of a rigid material such as polyethylene terephthalate ("PET"). In one embodiment, substrate 430 is made of flexible material such as polyimide or organic material. Substrate 430 may be disposed along an outer perimeter of contact lens 410 so as not to interfere with a viewable region of contact lens 410 that a wearer of contact lens 410 would be looking through. However, in one embodiment, substrate 430 is substantially transparent and does not substantially interfere with a wearer's view, regardless of disposition location.

In FIG. 4A, blink detection circuitry 231 (which may include a photodiode) is disposed in substrate 430 in a middle band of lens 410 such that when a wearer of lens 410 is viewing the world, the blink detection circuitry (and included photodiode) is exposed to ambient light. When the eye blinks, it covers blink detection circuitry 231, which changes the blink signal generated by blink detection circuitry 231. Contact lens 410 may be weighted (similar to contacts designed to correct astigmatism) to keep certain elements of contact lens 410 in their relative spatial orientations relative to the eye.

In FIG. 4A, gaze detection circuitry 232 is also disposed in substrate 430 and positioned in the middle band of contact lens 410. In addition, gaze detection circuitry 232 may be positioned closest to the nose of a wearer of lens 410. In one embodiment, gaze detection circuitry 232 includes a photodiode or an array of photodiodes. When an eye looks inward to focus at a near object/person/place, a photodiode included in gaze detection circuitry 232 may become covered by the eyelid, which changes a signal generated by the photodiode. In one embodiment, gaze detection circuitry 232 is similar to circuitry 310. In one embodiment, gaze detection circuitry 232 and blink detection circuitry 231 share electrical components, such as photodiodes. In other words, an array of photodiodes could be utilized to detect both blinking and inward gaze events. The electrical impedance scheme described above in association with blink detection circuitry 231 may also be utilized as gaze detection circuitry 232 to determine when the eye is gazing inwardly. As will be described in more detail below, detecting an inward gaze of the eye can be useful in adjusting an optical power for the eye to assist in near-field focusing.

Still referring to FIG. 4A, data transmission circuitry 235 is coupled to one or more electrodes 460 to send out electrical data signals onto the tear solution of the eye. Data reception circuitry 240 is also coupled to one or more electrodes 460 to receive the electrical data signals from the tear solution of the eye. The quantity and placement of electrodes will vary depending on whether a larger signal transmission/receptions is required, the ability to beamform the transmitted and received pulse path, whether the electrodes can be reused for impedance sensing, and the data protocol utilized. In one embodiment, only one electrode (e.g. 261) is used to drive the electrical data signals. In one embodiment, only one electrode (e.g. 263) is used to receive the electrical data signals as raw data signals from data transmission circuitry 235.

Figure 4B:
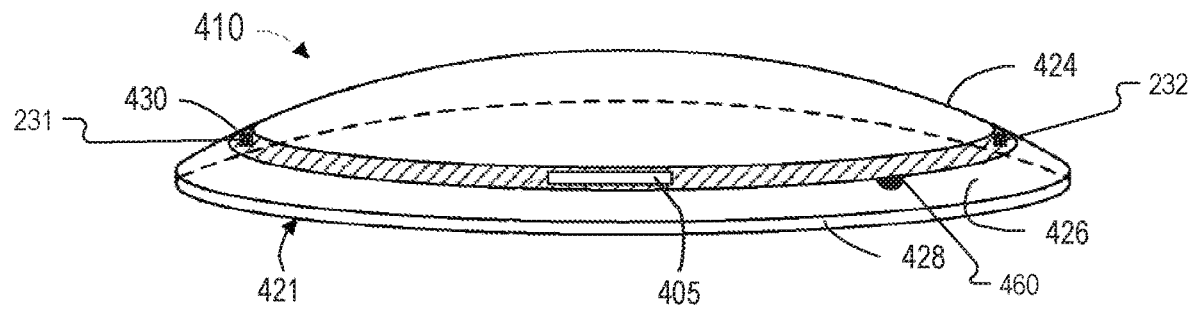
FIG. 4B illustrates a side view of the example contact lens of FIG. 4A, in accordance with an embodiment of the disclosure.

FIG. 4B illustrates a side view of contact lens 410 that includes logic engine 225, data transmission circuitry 235, data reception circuitry 240, blink detection circuitry 231, and gaze detection circuitry 232, in accordance with an embodiment of the disclosure. FIG. 4B shows transparent material 421 has a concave surface side 426 (eyeside) opposite a convex surface side 424 (external side). Concave surface side 426 will have substantial contact with the eye of a wearer of lens 410. A circular outside edge 428 connects concave surface side 426 and convex surface side 424. In FIG. 4B, a photodiode in blink detection circuitry 231 or gaze detection circuitry 232 will face outward so that it can measure ambient scene light. Any terminals to measure electrical impedance will be disposed on the external side 424 lens 410 in order to sense any eyelid covering contact 410 (in contrast to eyeside 426, which will be constantly contacting the eye). Electrode 460 and additional electrodes (not illustrated) are disposed on the eyeside of contact lens 410 so that the electrodes contact the tear film of the eye and thus access biopath 133.

Figure 5:
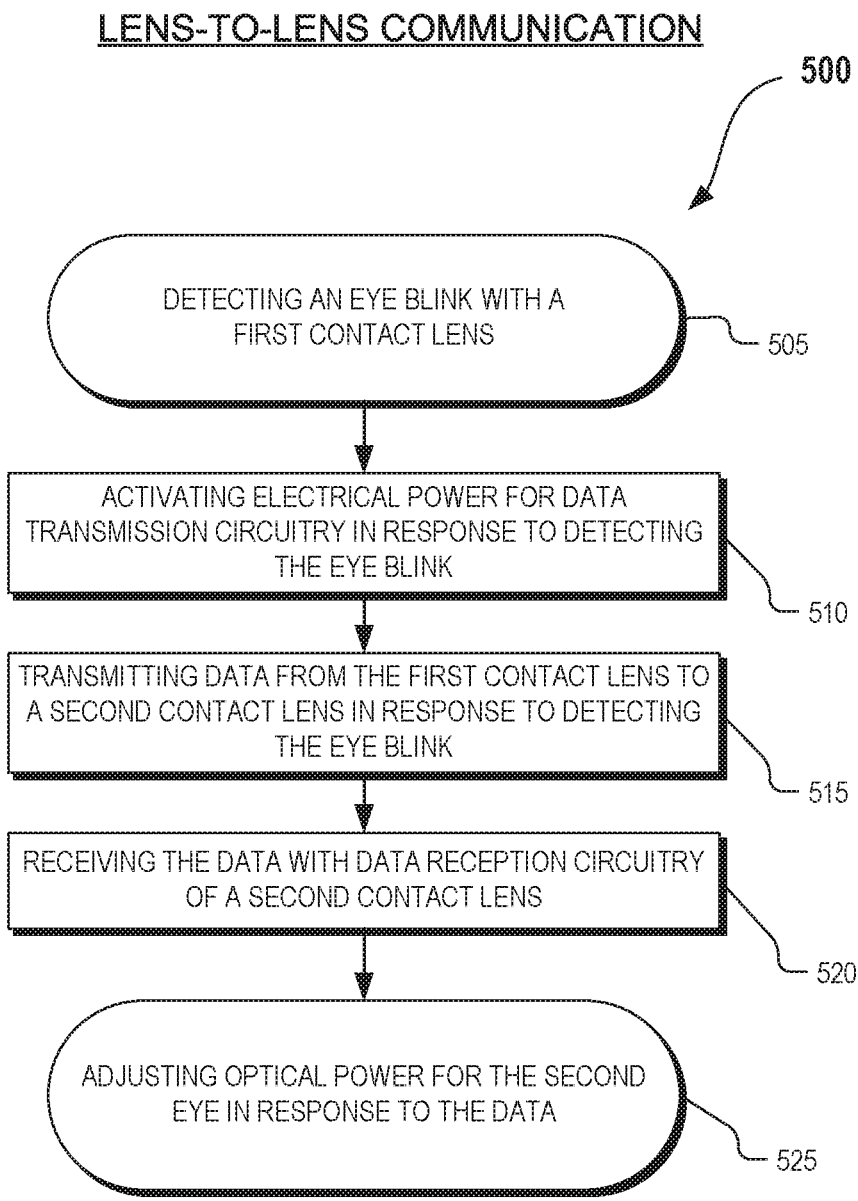
FIG. 5 illustrates a flow chart for an example process of lens-to-lens communication, in accordance with an embodiment of the disclosure.

FIG. 5 illustrates a flow chart for an example process 500 of lens-to-lens communication, in accordance with an embodiment of the disclosure. The order in which some or all of the process blocks appear in process 500 should not be deemed limiting. Rather, one of ordinary skill in the art having the benefit of the present disclosure will understand that some of the process blocks may be executed in a variety of orders not illustrated, or even in parallel.

In process block 505, an eye blink is detected with blink detection circuitry (e.g. 231A) included in a first contact lens (e.g. lens 150A). Electrical power for data transmission circuitry may be activated by in response to detecting the eye blink, in process block 510. Providing electrical power to data transmission circuitry 235 only after a blink is detected may save power compared to powering data transmission circuitry at all times. In process block 515, data is transmitted from the first contact lens (e.g. lens 150A) to a second contact lens (e.g. 150B) in response to detecting the eye blink. The data may take the form of electrical pulses that communicate digital words. The data is received with data reception circuitry (e.g. 240B) of the second contact lens (e.g. 150B) in process block 520. An optical power for the second eye is adjusted in response to the data in process block 525.

Figure 6:
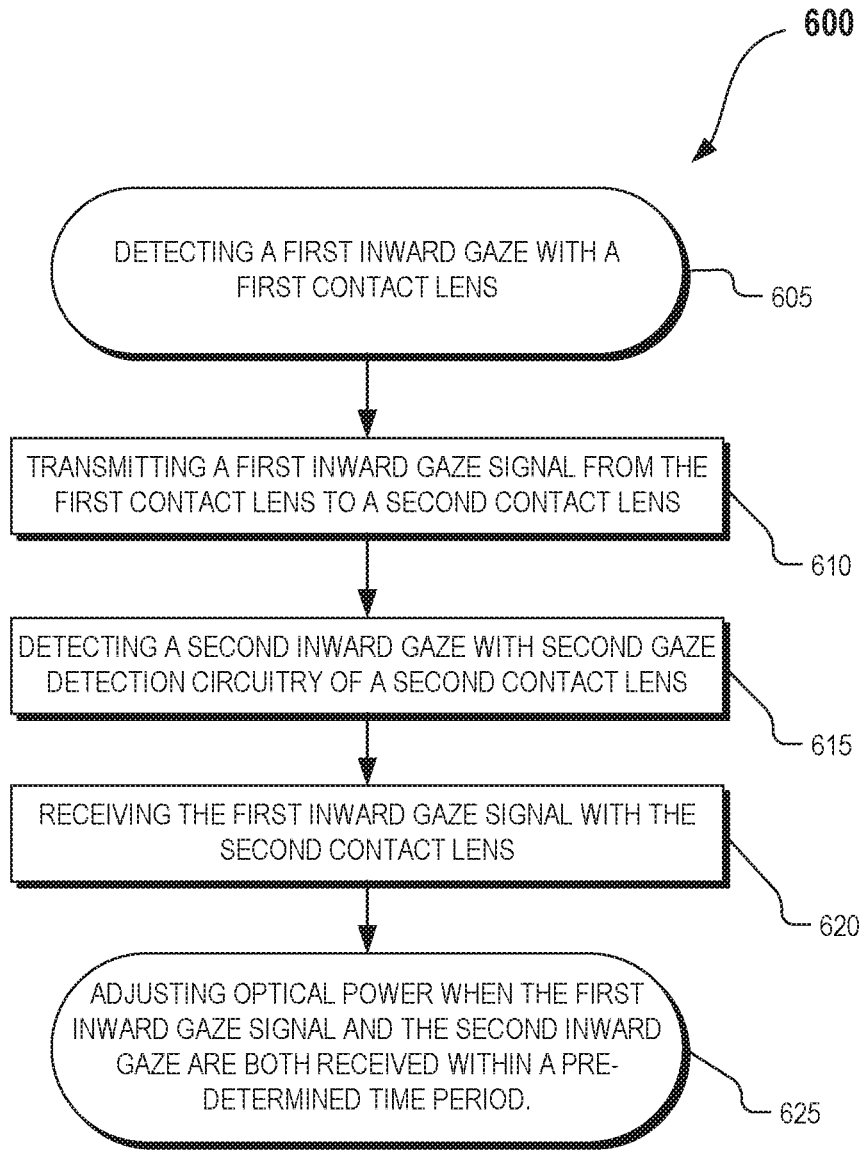
FIG. 6 illustrates a flow chart for an example process of detecting eye convergence using lens-to-lens communication, in accordance with an embodiment of the disclosure.

FIG. 6 illustrates a flow chart for an example process 600 of detecting eye convergence using lens-to-lens communication, in accordance with an embodiment of the disclosure.

The order in which some or all of the process blocks appear in process 600 should not be deemed limiting. Rather, one of ordinary skill in the art having the benefit of the present disclosure will understand that some of the process blocks may be executed in a variety of orders not illustrated, or even in parallel.

In process block 605, a first inward gaze is detected with first gaze detection circuitry (e.g. circuitry 232A) included in a first contact lens (e.g. lens 150A). In process block 610, a first inward gaze signal is transmitted from the first contact lens to a second contact lens (e.g. 150B) in response to detecting the first inward gaze. The first inward gaze signal may be a digital word sent in the form of voltage pulses via biopath 133 to the second contact lens. The first inward gaze signal may be sent by data transmission circuitry 235A, for example. A second inward gaze is detected with second gaze detection circuitry (e.g. circuitry 232B) included in the second contact lens, in process block 615. In process block 620, the second contact lens receives the first inward gaze signal from the first contact lens. The first inward gaze signal may be received by reception circuitry 240B, for example. An optical power for the second eye is adjusted when the first inward gaze signal is received within a pre-determined time period (e.g. 50 ms) from detecting the second inward gaze with the second gaze detection circuitry. The optical power may be changed by adjusting a control signal (e.g. voltage(s) signal) on a liquid crystal lens. The liquid crystal lens may be integrated into a contact lens, for example.

FIG. 7 illustrates a second flow chart for an example process 700 of detecting eye convergence using lens-to-lens communication, in accordance with an embodiment of the disclosure. Process 600 illustrates a unidirectional communication process while process 700 illustrates a bi-directional communication process. The order in which some or all of the process blocks appear in process 700 should not be deemed limiting. Rather, one of ordinary skill in the art having the benefit of the present disclosure will understand that some of the process blocks may be executed in a variety of orders not illustrated, or even in parallel.

In process block 705, inward gaze detection circuitry (e.g. circuitry 232B) is sampled for a left inward gaze signal. Process block 705 is executed until the left inward gaze signal is detected. In one example, a left inward gaze signal is detected when an output of a photodiode drops below a given threshold for a particular amount of time, which indicates that the photodiode is covered by an eyelid and thus, the left eye is looking inward and the wearer of the contact lens desires to focus on a near object (e.g. reading a book). If a left inward gaze is detected, process 700 proceeds to process block 710.

In process block 710, data transmission circuitry (e.g. 235B) is prepared to send an inward gaze signal to the right contact (e.g. lens 150A) via bio path 133. Preparing the data transmission circuitry may include powering up the data transmission circuitry and preloading it with the data (e.g. digital data) to be transmitted. Leaving the data transmission circuitry off except for when it is actually needed to transmit data will save power for executing other functions of the contact lens. If there is no blink within a time period T1 (e.g. 0.5 s), process 700 returns to process block 705. In one use context, the wearer of contact lenses 150A and 150B signals to the contact lenses that the user would like to adjust an optical power for their eyes by blinking soon after looking inward. This allows the contact lens to detect both the user looking inward and then blinking soon afterwards as a signal that the contact lens should initiate an optical power adjustment to facilitate near-field focus, for example.

If there is a blink detected within time period T1, process 700 proceeds from process block 710 to process block 715. In process block 715, the left inward gaze signal is transmitted to the right contact (e.g. lens 150A) via biopath 133. Also in process block 715, data reception circuitry 240 listens for a right inward gaze signal from the right contact. If the right inward gaze signal (acknowledgment) is not received by the left contact lens within a time period T2 (e.g. 200 ms), process 700 returns to process block 705. However, if right inward gaze signal (acknowledgment) is received by the left contact lens within time period T2, process 700 proceeds to process block 720 to adjust an optical power for the left eye.

When process block arrives at process block 720, a left inward gaze has been detected by the left contact lens and the left contact lens has received an acknowledgment (the right inward gaze signal) that the right contact has also detected a right inward gaze. Hence, the conclusion is that the left eye and the right eye are converging by both looking inward. The left contact has also received confirmation that the wearer of the contacts would like their optical power adjusted by way of detecting a blink within time T1 of detecting the left inward gaze. Process blocks 725, 730, 735, and 740 are similar (except adjusted to the right contact) to process blocks 705, 710, 715, and 720, respectively.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:
1. A contact lens comprising:
an adjustable lens disposed within the contact lens;
an electrode disposed within the contact lens and positioned to sense an electrical impedance indicative of an eyelid coverage of the contact lens;

an impedance measurement circuit disposed within the contact lens and coupled to the electrode to measure the electrical impedance indicative of the eyelid coverage; and control circuitry coupled to the impedance measurement circuit, the control circuitry including logic that, when executed by the control circuitry causes the contact lens to perform operations including:

detecting a first inward gaze of a first eye upon which the contact lens is mounted based upon the electrical impedance;

receiving, at the contact lens, a second inward gaze signal indicating a second eye has rotated to a second inward gaze; and adjusting an optical power of the adjustable lens when the second inward gaze signal is received within a pre-determined time period of detecting the first inward gaze of the first eye based upon the electrical impedance.

2. The contact lens of claim 1, wherein the control circuitry includes further logic that, when executed by the control circuitry, causes the contact lens to perform further operations, comprising:

transmitting a first inward gaze signal from the contact lens to another contact lens disposed on the second eye in response to detecting the first inward gaze.

3. The contact lens of claim 1, wherein the electrode is positioned within the contact lens to measure the electrical impedance as an impedance of a tear film of the first eye when the contact lens is disposed on the first eye.

4. The contact lens of claim 1, wherein the adjustable lens comprises a liquid crystal lens.

5. The contact lens of claim 1, further comprising data reception circuitry disposed within the contract lens and coupled to receive the second inward gaze signal via a biopath including tear solutions of the first eye and the second eye.

6. The contact lens of claim 1, further comprising:

blink detection circuitry disposed within the contact lens and coupled to the control circuitry, the blink detection circuitry configured to detect a blink of the first eye; and transmission circuitry disposed within the contact lens and coupled to the control circuitry, wherein the control circuitry includes further logic that, when executed causes the control lens to perform further operations comprises:

detecting the blink of the first eye with the blink detection circuitry; and transmitting a first inward gaze signal indicating the first inward gaze of the first eye when the first inward gaze is detected within a pre-determined time period of detecting the blink of the first eye.

7. A system comprising:

a first contact lens to mount on a first eye, the first contact lens comprising:

first gaze detection circuitry configured to generate a first inward gaze signal in response to the first eye looking inward;

one or more electrodes;

a logic engine coupled to receive the first inward gaze signal from the first gaze detection circuitry; and data transmission circuitry coupled between the one or more electrodes and the logic engine, wherein the logic engine causes the data transmission circuitry to drive electrical data signals onto the one or more electrodes in response to the first inward gaze signal; and a second contact lens to mount on a second eye, the second contact lens comprising:

one or more receiving electrodes disposed to receive the electrical data signals from the first contact lens via a biopath between the first and second eye;

a second logic engine; and data reception circuitry coupled to output data to the second logic engine in response to receiving the electrical data signals from the one or more receiving electrodes.

8. The system of claim 7, wherein the data reception circuitry includes:

a low noise amplifier (LNA) coupled to generate an amplified data signal in response to receiving the electrical data signals; and an analog correlator coupled to generate the output data in response to receiving the amplified data signal.

9. The system of claim 7, wherein the first gaze detection circuitry includes a photosensor coupled to generate an analog value as the first inward gaze signal in response to ambient light incident on the photosensor.

* * * * *